US 011065049B2

(12) United States Patent
Wang et al.

(10) Patent No.: US 11,065,049 B2
(45) Date of Patent: Jul. 20, 2021

(54) ELECTROSURGICAL DEVICE WITH ASYMMETRIC SEAL COMPRESSION

(71) Applicant: Gyrus ACMI, Inc., Southborough, MA (US)

(72) Inventors: Huisun Wang, Maple Grove, MN (US); Kester Batchelor, Mound, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 620 days.

(21) Appl. No.: 15/809,256

(22) Filed: Nov. 10, 2017

(65) Prior Publication Data
US 2019/0142503 A1    May 16, 2019

(51) Int. Cl.
*A61B 18/14*    (2006.01)
*A61B 18/00*    (2006.01)
(Continued)

(52) U.S. Cl.
CPC ...... *A61B 18/1445* (2013.01); *A61B 17/2909* (2013.01); *A61B 2017/2925* (2013.01);
(Continued)

(58) Field of Classification Search
CPC ........ A61B 18/1445; A61B 2017/2933; A61B 2018/1455; A61B 2017/2925; A61B 2017/2948; A61B 2018/00178; A61B 2090/034; A61B 2018/00077; A61B 2018/00404; A61B 17/2909; A61B 2018/0063; A61B 2018/00607; A61B 2018/00601; A61B 2018/00595; A61B 2018/00589
See application file for complete search history.

(56) References Cited

U.S. PATENT DOCUMENTS

| 763,226 A | 6/1904 | Walden et al. |
| 3,503,396 A | 3/1970 | Pierie et al. |

(Continued)

FOREIGN PATENT DOCUMENTS

| EP | 2554135 A1 | 2/2013 |
| WO | 2017123189 A1 | 7/2017 |

*Primary Examiner* — Michael F Peffley
*Assistant Examiner* — Yasamin Ekrami
(74) *Attorney, Agent, or Firm* — Schwegman Lundberg & Woessner, P.A.

(57) ABSTRACT

An end effector assembly of a forceps includes a first jaw member with a first sealing surface and a second sealing surface; a second jaw member with a first sealing surface and a second sealing surface, the first jaw member and the second jaw member being moveable relative to each other between an open position and a closed position, the first jaw member and the second jaw member including a blade slot defined therein and extending substantially along the first jaw member and the second jaw member, the first sealing surfaces being positioned on an opposite side of the blade slot than the second sealing surfaces; and a cutting blade that reciprocates in the blade slot. When the first jaw member and the second jaw member are in the closed position, the first sealing surfaces are separated by a first gap and the second sealing surfaces are separated by a second gap, the second gap being larger than the first gap.

25 Claims, 6 Drawing Sheets

(51) Int. Cl.
*A61B 17/29* (2006.01)
*A61B 90/00* (2016.01)

(52) U.S. Cl.
CPC .............. *A61B 2017/2933* (2013.01); *A61B 2017/2948* (2013.01); *A61B 2018/0063* (2013.01); *A61B 2018/00077* (2013.01); *A61B 2018/00178* (2013.01); *A61B 2018/00404* (2013.01); *A61B 2018/00589* (2013.01); *A61B 2018/00595* (2013.01); *A61B 2018/00601* (2013.01); *A61B 2018/00607* (2013.01); *A61B 2018/1455* (2013.01); *A61B 2090/034* (2016.02)

(56) References Cited

U.S. PATENT DOCUMENTS

| | | | |
|---|---|---|---|
| 5,728,121 A | 3/1998 | Bimbo et al. | |
| 5,752,973 A | 5/1998 | Kieturakis et al. | |
| 5,754,928 A | 5/1998 | Moe et al. | |
| 5,810,811 A * | 9/1998 | Yates | A61B 17/07207 606/50 |
| 6,086,586 A | 7/2000 | Hooven et al. | |
| 6,406,485 B1 | 6/2002 | Hossain et al. | |
| 6,500,176 B1 | 12/2002 | Truckai et al. | |
| 6,942,676 B2 | 9/2005 | Buelna | |
| 7,182,775 B2 | 2/2007 | de Guillebon et al. | |
| 7,276,068 B2 | 10/2007 | Johnson et al. | |
| 7,473,253 B2 | 1/2009 | Dycus et al. | |
| 8,192,433 B2 | 6/2012 | Johnson et al. | |
| 8,298,232 B2 | 10/2012 | Unger | |
| 8,317,787 B2 | 11/2012 | Hanna | |
| 8,382,754 B2 | 2/2013 | Odom et al. | |
| 8,597,297 B2 | 12/2013 | Couture et al. | |
| 8,647,343 B2 | 2/2014 | Chojin et al. | |
| 8,795,274 B2 | 8/2014 | Hanna | |
| 8,814,865 B2 * | 8/2014 | Reschke | A61B 18/1442 606/205 |
| 8,945,125 B2 | 2/2015 | Schechter et al. | |
| 9,526,564 B2 * | 12/2016 | Rusin | A61B 17/072 |
| 2008/0195093 A1 * | 8/2008 | Couture | A61B 18/1445 606/45 |
| 2009/0054894 A1 | 2/2009 | Yacht | |
| 2009/0149853 A1 | 6/2009 | Snields et al. | |
| 2011/0118736 A1 | 5/2011 | Harper et al. | |
| 2012/0059375 A1 | 3/2012 | Couture et al. | |
| 2013/0014375 A1 | 1/2013 | Hempstead et al. | |
| 2013/0030433 A1 * | 1/2013 | Heard | A61B 18/1442 606/45 |
| 2018/0360525 A1 * | 12/2018 | Batchelor | A61B 18/1445 |

\* cited by examiner

ELECTROSURGICAL DEVICE WITH ASYMMETRIC SEAL COMPRESSION

FIELD

The present disclosure relates to an electrosurgical device. More specifically, the present disclosure relates to an electrosurgical device for vessel sealing.

BACKGROUND

Generally forceps may be utilized for laparoscopic surgery. The forceps may be employed to control delicate movements inside a patient and may include a gripping assembly or a cutting assembly. Further, the forceps may utilize electrical energy in the gripping assembly. Typically, the forceps have a pair of opposed resilient jaws that are closed against each other by pulling the jaws into a distal end of a shaft that captures a portion of the jaws that is wider than the distal end opening of the shaft so that the jaws are moved together. Similarly the shaft may be pushed over the jaws so that the jaws are moved together to create a gripping force. In both of these arrangements, the shaft captures the jaws and acts as a cam that forces the jaws together to create the gripping force.

Current bipolar electrosurgical sealing forceps employ a pair of jaws with RF energy to coagulate a vessel and further employ a moveable cutting blade to cut the sealed vessel after coagulation, for example, during the removal of an organ from a patient. In such procedures, one portion of the cut vessel remains attached to the patient's vascular system, while the other portion of the cut vessel is removed with the organ. Typically, electrosurgical sealing energy is applied equally to the patient side of the vessel and to the resected portion of the vessel. This approach, however, does not address the higher blood pressures that occur in the patient side vessel seal, while the resected vessel seal need only prevent incidental leakage from the resected organ.

Thus, while current electrosurgical forceps achieve their intended purpose, there is a need for a forceps with asymmetrical compression capabilities.

SUMMARY

The present disclosure provides an end effector assembly with asymmetric seal compression for vessel sealing.

Accordingly, pursuant to one aspect of the present invention, an end effector assembly of a forceps includes a first jaw member with a first sealing surface and a second sealing surface; a second jaw member with a first sealing surface and a second sealing surface, the first jaw member and the second jaw member being moveable relative to each other between an open position and a closed position, the first jaw member and the second jaw member including a blade slot defined therein and extending substantially along the first jaw member and the second jaw member, the first sealing surfaces being positioned on an opposite side of the blade slot than the second sealing surfaces; and a cutting blade that reciprocates in the blade slot. When the first jaw member and the second jaw member are in the closed position, the first sealing surfaces are separated by a first gap and the second sealing surfaces are separated by a second gap, the second gap being larger than the first gap.

The foregoing aspect of the present invention can be further characterized by one or any combination of the features described herein, such as: the blade slot is closer to a lateral side of the larger gap; the blade slot is closer to the lateral side of the smaller gap; the first jaw member and the second jaw member rotate relative to each other; at least one of the first sealing surface and the second sealing surface of at least one of the first jaw member and the second jaw member is an electrically conductive surface configured to connect to an electrosurgical energy source that generates energy to coagulate tissue grasped between the first jaw member and the second jaw member; at wherein both of the first sealing surface and the second sealing surface of at least one of the first jaw member and the second jaw member are an electrically conductive surface configured to connect to the electrosurgical energy source; both of the first sealing surface and the second sealing surface of both the first jaw member and the second jaw member are an electrically conductive surface configured to connect to the electrosurgical energy source; the end effector assembly further includes at least one non-conductive stop positioned on either side of the blade slot; and the end effector assembly further includes one or more first non-conductive stops positioned on one side of the blade slot and one or more second non-conductive stops positioned on the other side of the blade slot, the first non-conductive stops having a different thickness than the second non-conductive stops.

Accordingly, pursuant to another aspect of the present invention, a forceps includes at least one shaft that includes an end effector assembly at a distal end thereof. The end effector assembly includes a first jaw member with a first sealing surface and a second sealing surface; a second jaw member with a first sealing surface and a second sealing surface, the first jaw member and the second jaw member being moveable relative to each other between an open position and a closed position, the first jaw member and the second jaw member including a blade slot defined therein and extending substantially along the first jaw member and the second jaw member, the first sealing surfaces being positioned on an opposite side of the blade slot than the second sealing surfaces; and a cutting blade that reciprocates in the blade slot. When the first jaw member and the second jaw member are in the closed position, the first sealing surfaces are separated by a first gap and the second sealing surfaces are separated by a second gap, the second gap being larger than the first gap.

The foregoing aspect of the present invention can be further characterized by one or any combination of the features described herein, such as: the blade slot is closer to a lateral side of the larger gap; the blade slot is closer to the lateral side of the smaller gap; the first jaw member and the second jaw member rotate relative to each other; at least one of the first sealing surface and the second sealing surface of at least one of the first jaw member and the second jaw member is an electrically conductive surface configured to connect to an electrosurgical energy source that generates energy to coagulate tissue grasped between the first jaw member and the second jaw member; both of the first sealing surface and the second sealing surface of at least one of the first jaw member and the second jaw member are an electrically conductive surface configured to connect to the electrosurgical energy source; both of the first sealing surface and the second sealing surface of both the first jaw member and the second jaw member are an electrically conductive surface configured to connect to the electrosurgical energy source; the forceps further includes at least one non-conductive stop positioned on either side of the blade slot; and the forceps further includes one or more first non-conductive stops positioned on one side of the blade slot and one or more second non-conductive stops positioned on the other side of the blade slot, the first non-conductive stops having a different thickness than the second non-conductive stops.

Accordingly, pursuant to another aspect of the present invention, a method of using forceps includes opening a first jaw member and a second jaw member, the first jaw member having a first sealing surface and a second sealing surface and the second jaw member having a first sealing surface and a second sealing surface, the first jaw member and the second jaw member including a blade slot defined therein and extending substantially along the first jaw member and the second jaw member, the first sealing surfaces being positioned on an opposite side of the blade slot than the second sealing surfaces; closing the first jaw member and the second jaw member to grasp tissue therebetween, when the first jaw member and the second jaw member are in the closed position, the first sealing surfaces being separated by a first gap and the second sealing surfaces being separated by a second gap, the second gap being larger than the first gap; and moving a cutting blade along the blade slot to cut the tissue grasped between the first jaw member and the second jaw member.

The method of using the forceps may be further characterized by one or any combination of the following features: the blade slot is closer to a lateral side of the larger gap; the blade slot is closer to the lateral side of the smaller gap; at least one of the first sealing surface and the second sealing surface of at least one of the first jaw member and the second jaw member is an electrically conductive surface connected to an electrosurgical energy source; the method further includes generating electrical energy from the electrosurgical energy source to coagulate tissue grasped between the first jaw member and the second jaw member; both of the first sealing surface and the second sealing surface of at least one of the first jaw member and the second jaw member are an electrically conductive surface configured to connect to the electrosurgical energy source; and both of the first sealing surface and the second sealing surface of both the first jaw member and the second jaw member are an electrically conductive surface configured to connect to the electrosurgical energy source.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

Figure 1:
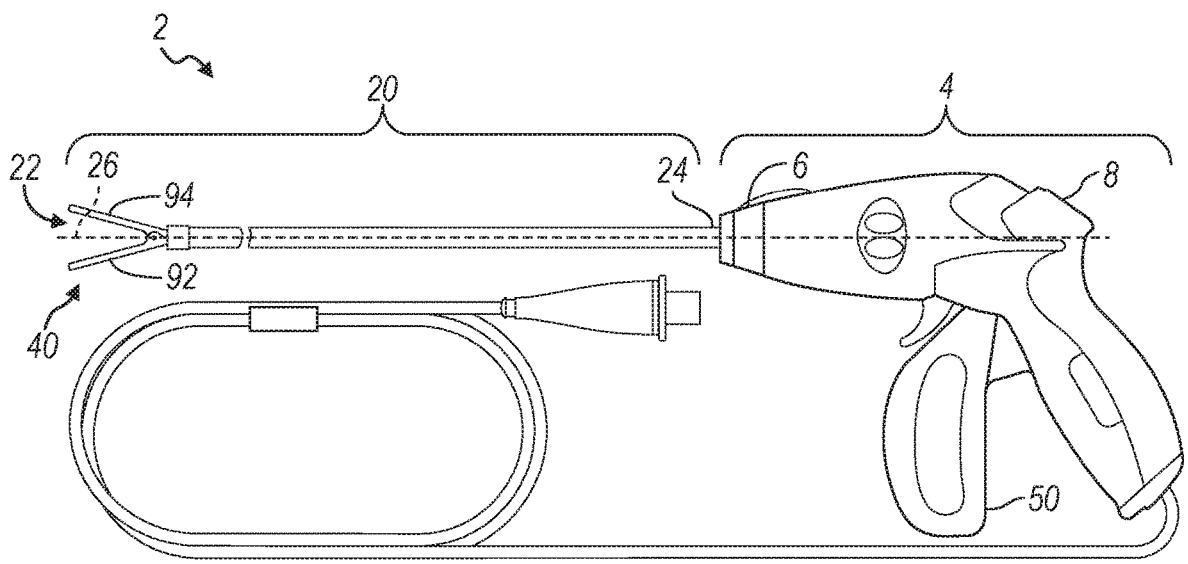
FIG. 1 illustrates an electrosurgical forceps in accordance with the principles of the present invention.

The following description is merely exemplary in nature and is not intended to limit the present disclosure, application, or uses.

The following description is merely exemplary in nature and is not intended to limit the present disclosure, application, or uses.

Referring now to the drawings, a forceps, such as, for example, a laparoscopic forceps, embodying the principles of the present invention is illustrated therein and designated at 2. The forceps 2 may function to grip an object. The forceps 2 may be used during surgery to grip a feature of interest including: a part of a body, an anatomical feature, tissue, veins, arteries, or a combination thereof. The forceps 2 may function to be used in surgery, for example, laparoscopic surgery. The forceps 2 may be used with or without power. Current may be passed through the forceps 2 so that the forceps are used for electrosurgery. For example, a therapy current may be passed from one jaw to a second jaw when tissue is located within the jaw and the therapy current may coagulate blood, cauterize, cut, or a combination thereof. The forceps 2 may generally include one or more working assemblies and sufficient controls to work the one or more assemblies. The forceps 2 may include parts employed to perform the recited functions and may include generally, a stylet (e.g., a tubular member, a hollow tube, or an assembly of tubes), a hand piece, one or more operable mechanisms used to actuate the stylet, or a combination thereof. The hand piece may be an assembly of parts or housing structures capable of forming a hand piece structure with a cavity. Note that the present invention is not limited to laparoscopic procedures. That is, the below described jaws can be employed with any type of medical device that clamps onto tissue.

Turning now to FIG. 1, a side view of the forceps 2 is shown. The forceps 2 include a handpiece 4 having a distal end 6 and a proximal end 8. The handpiece 4 also includes at least one operable mechanism 50. A tubular member 20 has a proximal end 24 that is connected to the distal end 6 of the handpiece 4. The tubular member 20 includes a distal end 22 that includes jaws 40 extending therefrom. The jaws 40 have members 92 and 94 that open and close when the tubular member 20 is moved forward along the longitudinal axis 26 of the tubular member into contact with the members 92 and 94 or the jaws 40 are moved backwards along the longitudinal axis 26 into contact with the tubular member 20.

Figure 2:
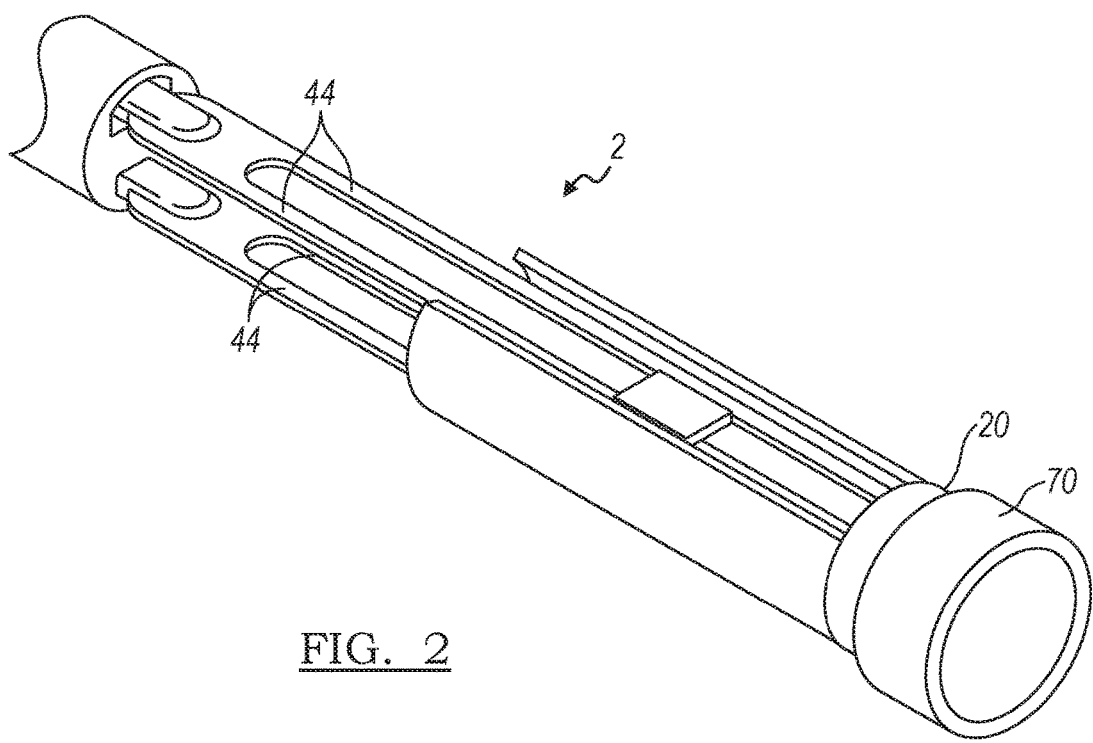
FIG. 2 illustrates an expanded interior view of a tubular member for the forceps.
Figure 6:
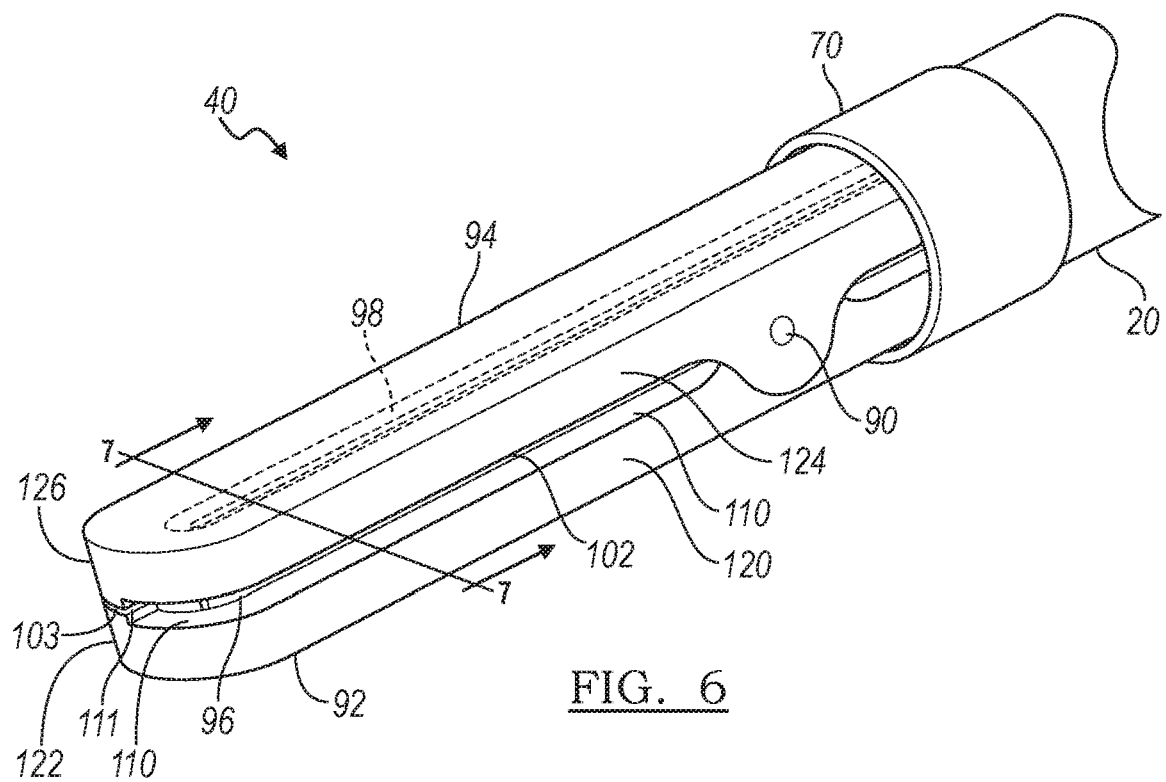
FIG. 6 illustrates a perspective view of a set of jaws for the forceps shown in FIG. 1.
Figure 7:
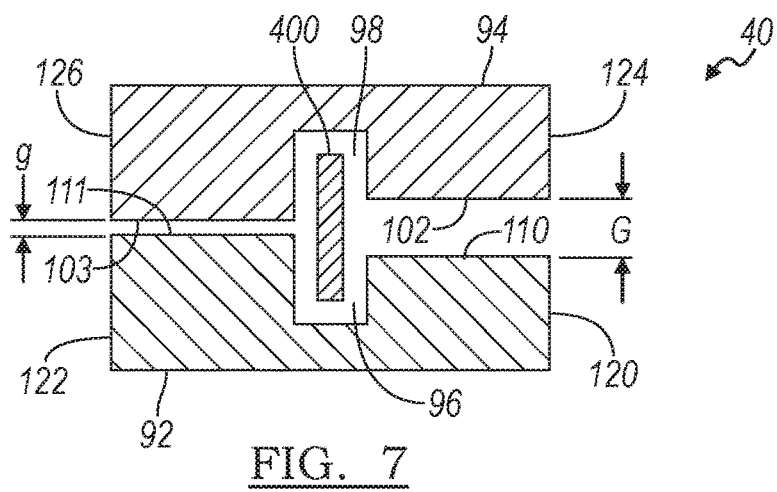
FIG. 7 illustrates a cross-sectional view of the set of jaws shown in FIG. 6.

Referring further to FIGS. 2, 6 and 7, a camming shaft 70 is located on the forceps 2 with the jaws 40 extending therefrom. The members 92 and 94 are biased by the camming shaft 70 so that the jaws 40 are opened and closed. The members 92 and 94 include a pair of slots 96 and 98 that extend through the members 92 and 94, respectively. The jaw member 92 includes a first sealing surface 110 that extends from a lateral surface 120 to the slot 96 and a second sealing surface 111 that extends from a lateral surface 122 to the slot 96. The jaw member 94 includes a first sealing surface 102 that extends from a lateral surface 124 to the slot 98 and a second sealing surface 103 that extends from a lateral surface 126 to the slot 98. When the jaw members 92 and 94 are in a closed position, the sealing surfaces 103 and 111 define a first compression zone with a gap, g, and the sealing surfaces 102 and 110 define a second compression zone with a gap, G, that is larger than the gap, g.

Figure 3:
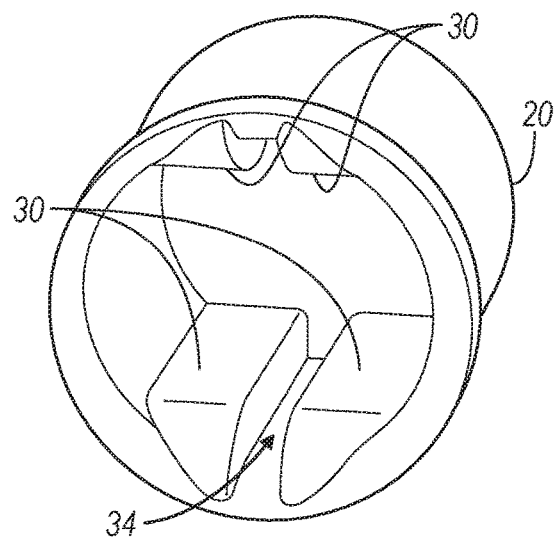
FIG. 3 illustrates an end view of the tubular member.

FIG. 3 illustrates the end of the tubular member 20 or a camming shaft showing a pair of internal flat portions 30 along the top surfaces and the bottom surfaces. A blade recess 34 extends between the pair of internal flat portions 30 so that a blade 400 (FIGS. 15 and 16) extends out of the tubular member 20 and reciprocates in the slots 96 and 98.

Figure 4:
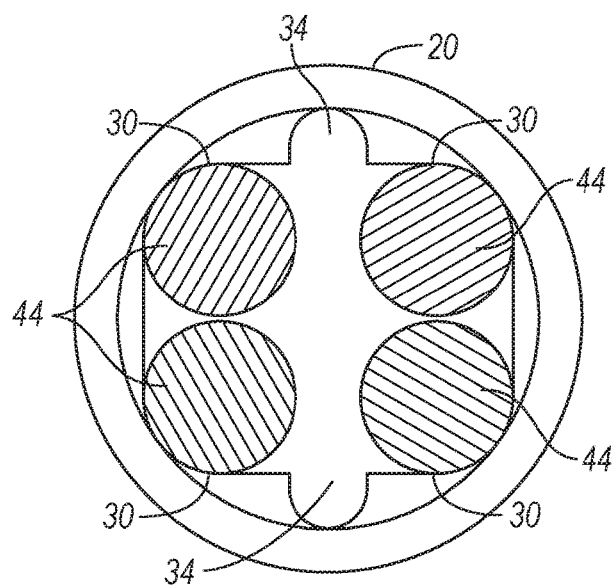
FIG. 4 illustrates a cross-sectional view of the tubular member.

FIG. 4 illustrates a cross-sectional view of a tubular member 20. The internal flat portions 30 include at least a portion that has a complementary shape to that of a set of legs 44 (FIG. 2) of the jaws 40. Accordingly, as the tubular member 20 or the legs 44 axially move, the internal flat portions 30 control the orientation and movement of the jaws.

Figure 5:
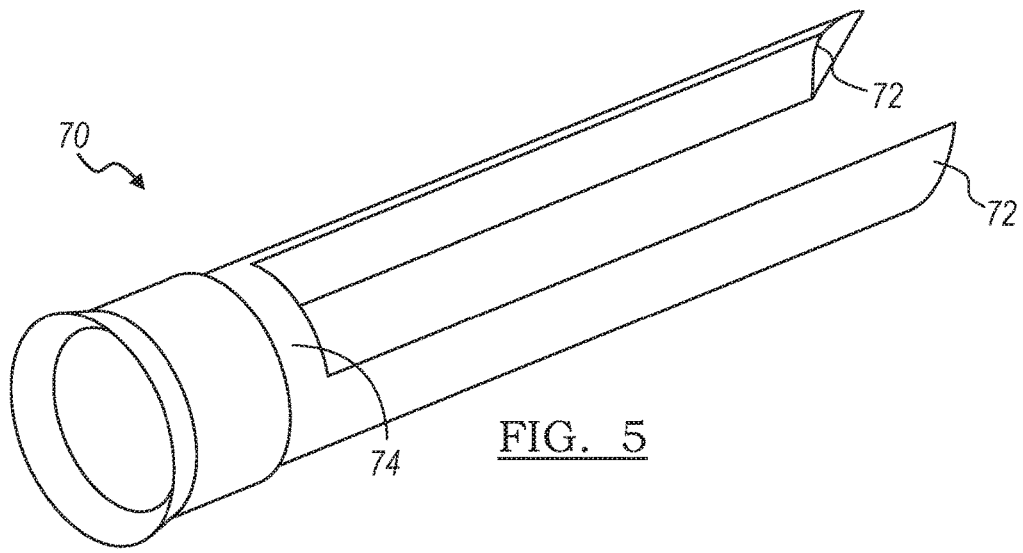
FIG. 5 illustrates a perspective view of a camming shaft of the tubular member.

FIG. 5 illustrates a perspective view of one example of a camming shaft 70 that is inserted into the tubular member 20. The camming shaft 70 includes a molded flare 74 with a pair of protrusions 72 extending therefrom.

FIG. 6 illustrates the jaws 40 including a pin 90 located between the jaws. The pin 90 holds the jaw members 92 and 94 together and provide a pivot point for the jaw members 92 and 94 such that the members 92 and 94 close when the tubular member 20 is slid over the opposing members 92 and 94.

In various arrangements, the jaw members 92 and 94 can be electrical connected to a generator that provides a source of electrosurgical energy so that a RF voltage with different potentials can be applied to the electrically connected sections of the jaw members 92 and 94. The RF voltage produces a current that passes from one jaw member to the other jaw member electrode through tissue, thereby heating the tissue to coagulate or cut the tissue.

Figure 15:
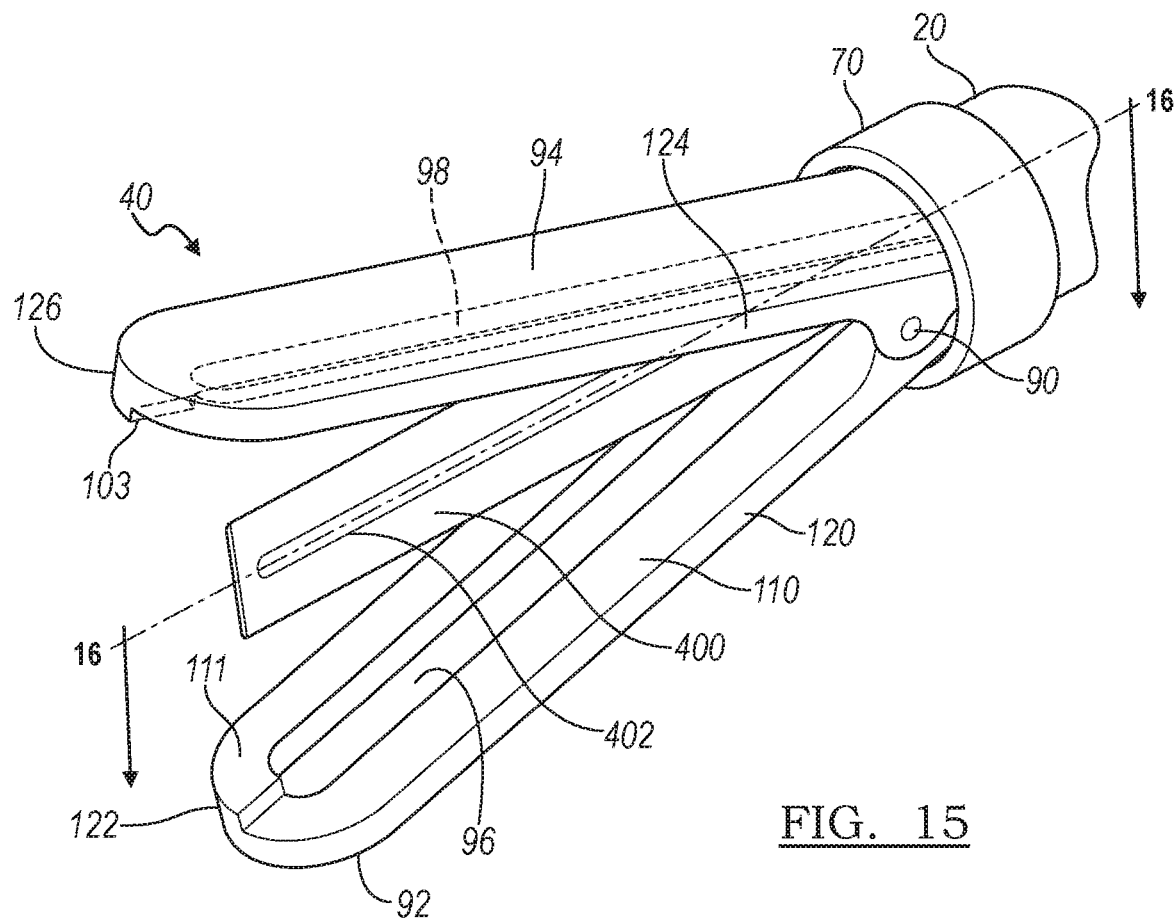
FIG. 15 illustrates a perspective view of the jaws shown in FIG. 6 with a cutting blade.
Figure 16:
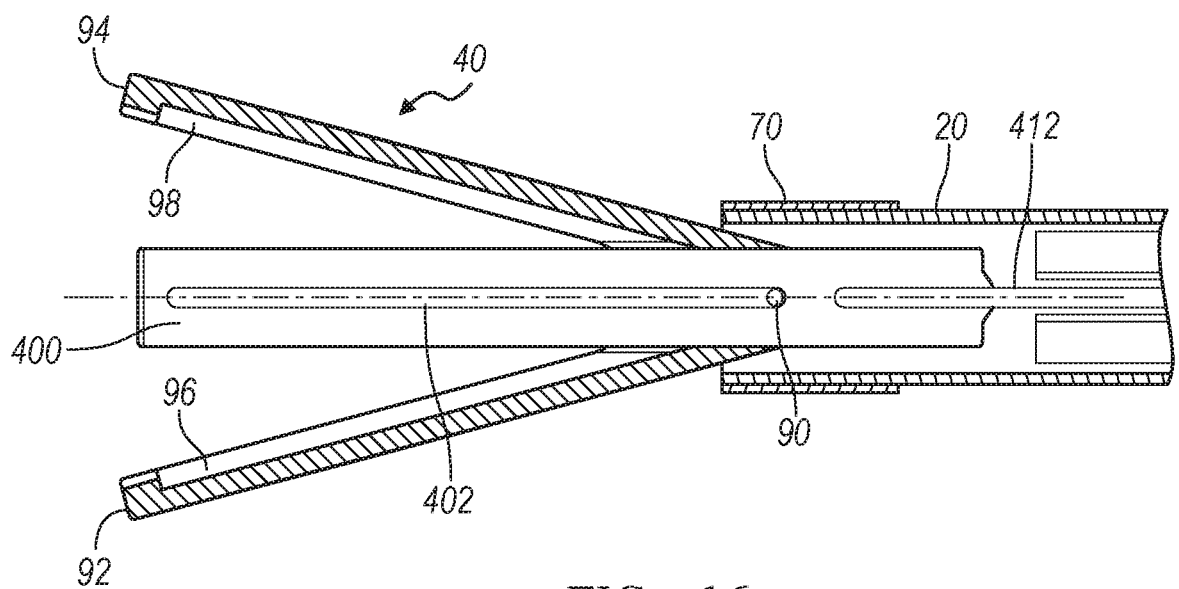
FIG. 16 illustrates a side view of the jaws shown in FIG. 6 with the cutting blade.

The jaw arrangement 40 can include a cutting blade. For example, as shown in FIGS. 15 and 16, the jaws 40 are shown with a blade 400. The blade 400 includes a slot 402 that engages with the pin 90 to allow the blade 400 to reciprocate along the pin 90. The blade 400 is connected to a blade shaft 412. Hence, axial movement of the blade shaft 412 results in reciprocating axial movement of the blade 400 along the slots 96 and 98 of the jaw members 92 and 94 to cut tissue clamped between the jaw members 92 and 94.

Figure 8:
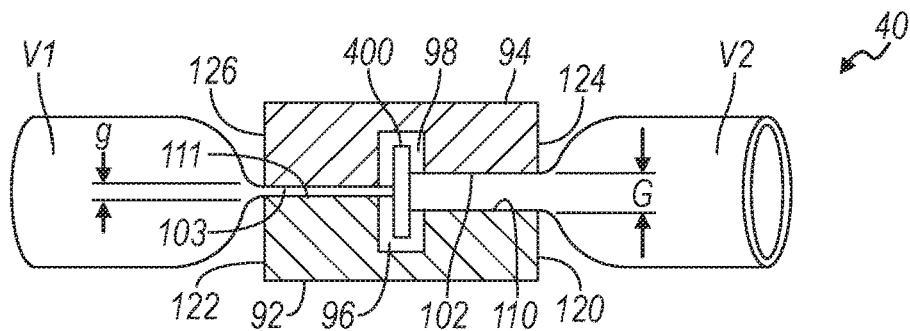
FIG. 8 illustrates a cross-section view of the set of jaws gripping a vessel.

Turning now to FIG. 8, the jaw members 92 and 94 are shown clamping a vessel with a patient side, V1, and an organ side, V2. Typically, the patient side vessel, V1, is under higher blood pressure than the organ side, V2. The jaw members 92 and 94 are arranged such that The compression zone with the smaller gap, g, creates a higher compression and stronger seal on the patient side vessel, V1, and the compression zone with the larger gap, G, creates a lower compression seal on the organ side vessel, V2, since the resected vessel seal need only prevent incidental leakage from the resected organ.

Figure 9:
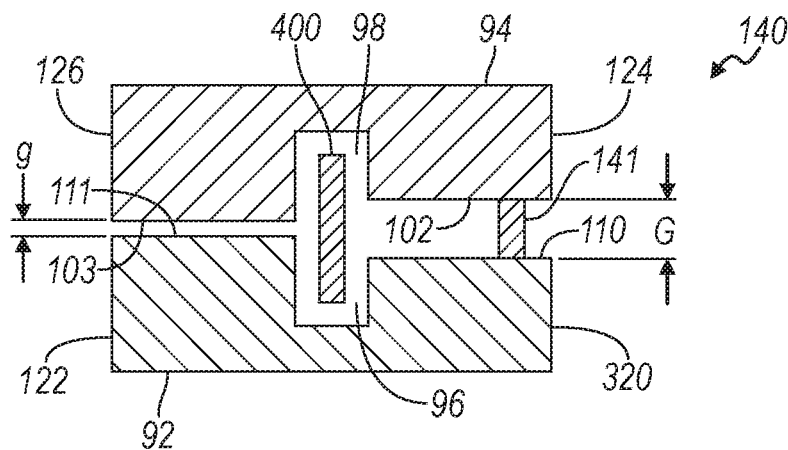
FIG. 9 illustrates a cross-sectional view of an alternative set of jaws in accordance with the principles of the present invention.
Figure 10:
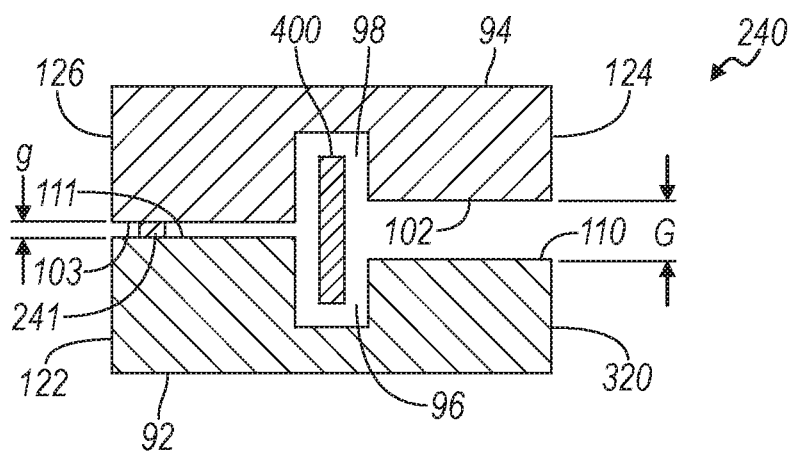
FIG. 10 illustrates a cross-sectional view of yet another alternative set of jaws in accordance with the principles of the present invention.

Turning now to FIG. 9, there is shown a set of jaws 140 with one or more non-conductive stops 141 positioned between the sealing surfaces 102 and 110 to prevent shorting the electrically portions of the jaw members 92 and 94. Alternatively, as shown in FIG. 10, a set of jaws 240 includes one or more non-conductive stops 241 positioned between the sealing surfaces 103 and 111 to prevent shorting the electrically portions of the jaw members 92 and 94. In yet another arrangement, the aforementioned jaw arrangements can include one or more non-conductive stops positioned between the sealing surfaces 102 and 110 and one or more non-conductive stops positioned between the sealing surfaces 103 and 111, the one or more stops positioned between the sealing surfaces 102 and 110 having a greater thickness than the one or more stops positioned between the sealing surfaces 103 and 111.

Figure 11:
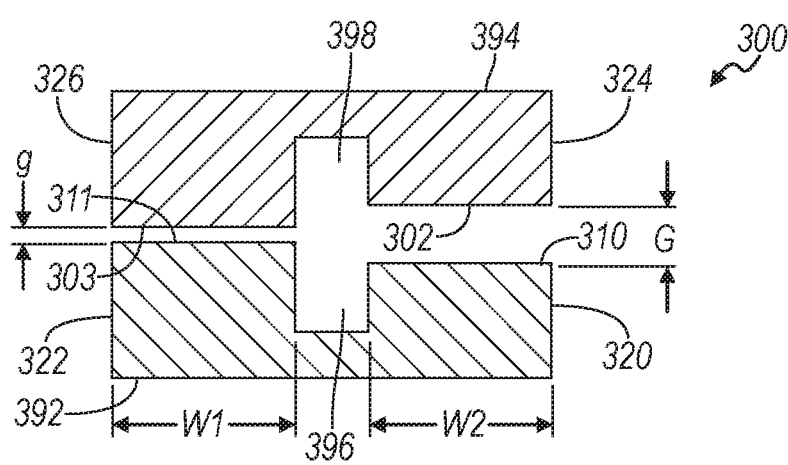
FIG. 11 illustrates a cross-sectional view of yet another alternative set of jaws in accordance with the principles of the present invention.

Referring now to FIG. 11, there is shown an alternative set of jaws 300 with a first jaw member 392 and a second jaw member 394. The members 392 and 394 include a pair of slots 396 and 398 that extend through the members 392 and 394, respectively. The jaw member 392 includes a first sealing surface 310 that extends from a lateral surface 320 to the slot 396 and a second sealing surface 311 that extends from a lateral surface 322 to the slot 396. The jaw member 394 includes a first sealing surface 302 that extends from a lateral surface 324 to the slot 398 and a second sealing surface 303 that extends from a lateral surface 326 to the slot 398. When the jaw members 392 and 394 are in a closed position, the sealing surfaces 303 and 311 define a first compression zone with a gap, g, and the sealing surfaces 302 and 310 define a second compression zone with a gap, G. The compression zone with a gap, g, has a width, W1, and the compression zone with a gap, G, has a width, W2. In some arrangements, the widths W1 and W2 are equal, while in other arrangements the width, W1, is greater than or less than the width, W2.

Figure 12:
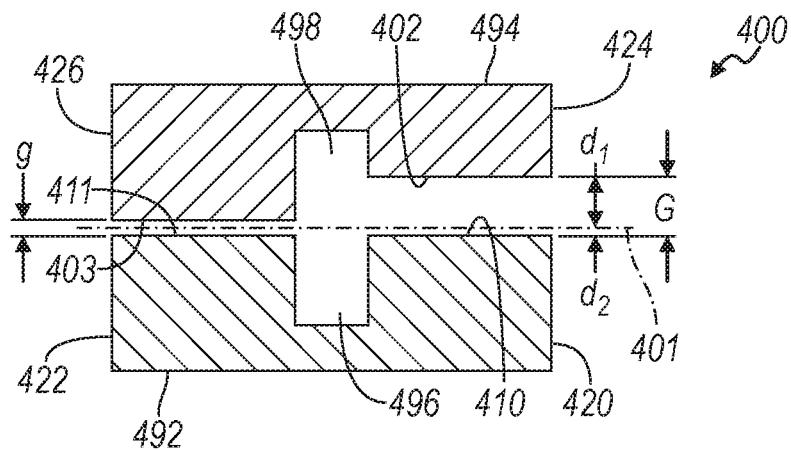
FIG. 12 illustrates a cross-sectional view of yet another alternative set of jaws in accordance with the principles of the present invention.

Turning to FIG. 12, there is shown an alternative jaw arrangement 400 with a first jaw member 492 and a second jaw member 494. The members 492 and 494 include a pair of slots 496 and 498 that extend through the members 492 and 494, respectively. The jaw member 492 includes a first sealing surface 410 that extends from a lateral surface 420 to the slot 496 and a second sealing surface 411 that extends from a lateral surface 422 to the slot 396. The jaw member 494 includes a first sealing surface 402 that extends from a lateral surface 424 to the slot 498 and a second sealing surface 403 that extends from a lateral surface 426 to the slot 498. When the jaw members 492 and 494 are in a closed position, the sealing surfaces 403 and 411 define a first compression zone with a gap, g, and the sealing surfaces 402 and 410 define a second compression zone with a gap, G. In the arrangement shown in FIG. 12, the gap, G, is off-centered with respect to a center line 401. That is, the gap, G, has a first distance, d1, that extends between the sealing surface 402 and the centerline 401 and a second distance, d2, that extends between the sealing surface 410 and the centerline 401. The distance, d1, can be greater than or less than the distance, d2.

Figure 13:
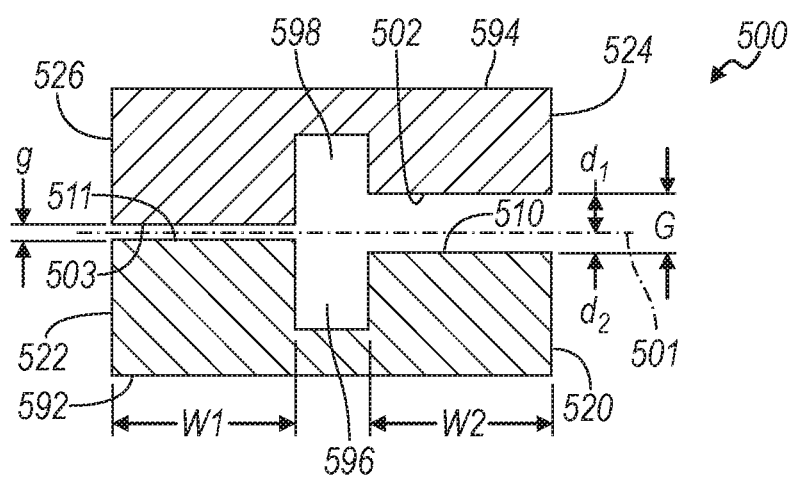
FIG. 13 illustrates a cross-sectional view of yet another alternative set of jaws in accordance with the principles of the present invention.
Figure 14:
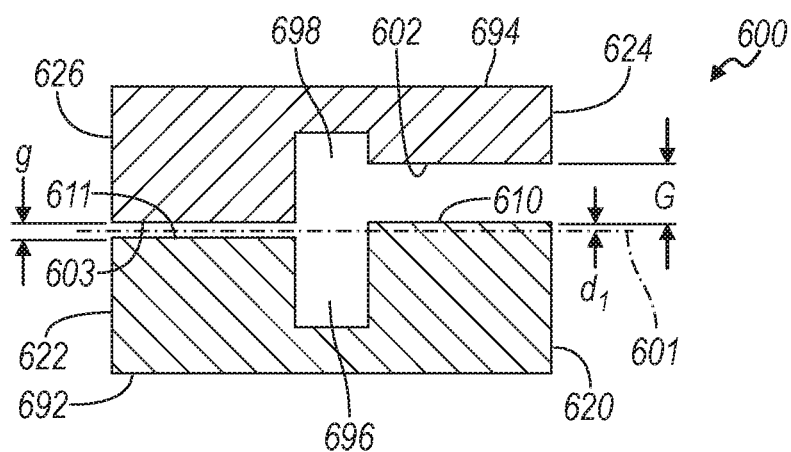
FIG. 14 illustrates a cross-sectional view of yet another alternative set of jaws in accordance with the principles of the present invention.

Turning to FIG. 13, there is shown yet another jaw arrangement 500 with a first jaw member 592 and a second jaw member 594. The members 592 and 594 include a pair of slots 596 and 598 that extend through the members 592 and 594, respectively. The jaw member 592 includes a first sealing surface 510 that extends from a lateral surface 520 to the slot 596 and a second sealing surface 511 that extends from a lateral surface 522 to the slot 596. The jaw member 594 includes a first sealing surface 502 that extends from a lateral surface 524 to the slot 598 and a second sealing surface 503 that extends from a lateral surface 526 to the slot 598. When the jaw members 592 and 594 are in a closed position, the sealing surfaces 503 and 511 define a first compression zone with a gap, g, and the sealing surfaces 502 and 510 define a second compression zone with a gap, G. In the arrangement shown in FIG. 13, the gap, G, is off-centered with respect to a center line 501. That is, the gap, G, has a first distance, d1, that extends between the sealing surface 502 and the centerline 501 and a second distance, d2, that extends between the sealing surface 510 and the centerline 501. The distance, d1, can be greater than or less than the distance, d2. Note further that the compression zone with a gap, g, has a width, W1, and the compression zone with a gap, G, has a width, W2. In some arrangements, the widths W1 and W2 are equal, while in other arrangements the width, W1, is greater than or less than the width, W2, Referring now to FIG. 14, there is shown yet another jaw arrangement 600 with a first jaw member 692 and a second jaw member 694. The members 692 and 694 include a pair of blade slots 696 and 698 that extend through the members 692 and 694, respectively. The jaw member 692 includes a first sealing surface 610 that extends from a lateral surface 620 to the slot 696 and a second sealing surface 611 that extends from a lateral surface 622 to the slot 696. The jaw member 694 includes a first sealing surface 602 that extends from a lateral surface 624 to the slot 698 and a second sealing surface 603 that extends from a lateral surface 626 to the slot 698. When the jaw members 692 and 694 are in a closed position, the sealing surfaces 603 and 611 define a first compression zone with a gap, g, and the sealing surfaces 602 and 610 define a second compression zone with a gap, G. In the arrangement shown in FIG. 14, the gap, G, is off-centered with respect to a center line 501. That is, the entire gap, G, is offset by a distance, d1, from the centerline 601.

In various arrangements, the jaw members of the jaw arrangements 140, 240, 300, 400, 500 and 600 can be electrical connected to a generator that provides a source of electrosurgical energy so that a RF voltage with different potentials can be applied to the electrically connected sections of the jaw members. The RF voltage produces a current that passes from one jaw member to the other jaw member electrode through tissue, thereby heating the tissue to coagulate or cut the tissue. Further, any of the jaw arrangements 140, 240, 300, 400, 500 and 600 described previously can include the cutting blade 400 described previously for the jaw arrangement 40. The jaw arrangements 300, 400, 500 and 600 can include the non-conductive stops described previously for the jaw arrangements 140 and 240.

Although the previously described jaws were directed to one jaw member pivotally attached to another jaw member, the present invention contemplates any type of jaw member that clamps onto tissue with another jaw member. For example, the jaw members can clamp onto tissue as the jaw members move toward each other in any suitable manner including translational and rotational movement; that is, the distal section can rotate or translate relative to the proximal section. Further, as mentioned previously, various components of the any of the above-described jaw members can be electrically conductive. The components themselves can be electrically conductive electrodes or electrically conductive material can be added to the component to form an electrode on the component. Any of the above described jaw members can have teeth for gripping tissue.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. An end effector assembly of a forceps comprising:
a first jaw member with a first sealing surface and a second sealing surface;
a second jaw member with a first sealing surface and a second sealing surface, the first jaw member and the second jaw member being movable relative to each other between an open position and a closed position, the first jaw member and the second jaw member including a blade slot defined therein and extending substantially along the first jaw member and the second jaw member, the first sealing surfaces being positioned on an opposite side of the blade slot than the second sealing surfaces; and
a cutting blade that reciprocates in the blade slot,
wherein when the first jaw member and the second jaw member are in closed position, the first sealing surface of the first jaw member and the first sealing surface of the second jaw member are separated by a first constant, uniform gap extending continuously from the blade slot to a first lateral side of the first and second jaw members and the second sealing surface of the first jaw member and the second sealing surface of the second jaw member are separated by a second constant, uniform gap extending continuously from the blade slot to a second lateral side of the first and second jaw members, the second constant, uniform gap being larger than the first constant, uniform gap.

2. The end effector assembly for claim 1 wherein the blade slot is closer to the second lateral side of the second constant, uniform gap.

3. The end effector assembly for claim 1 wherein the blade slot is closer to the first lateral side of the first constant, uniform gap.

4. The end effector assembly of claim 1 wherein the first jaw member and the second jaw member rotate relative to each other.

5. The end effector assembly of claim 1 wherein at least one of the first sealing surface and the second sealing surface of at least one of the first jaw member and the second jaw member is an electrically conductive surface configured to connect to an electrosurgical energy source that generates energy to coagulate tissue grasped between the first jaw member and the second jaw member.

6. The end effector assembly of claim 5 wherein both of the first sealing surface and the second sealing surface of at least one of the first jaw member and the second jaw member are an electrically conductive surface configured to connect to the electrosurgical energy source.

7. The end effector assembly of claim 6 wherein both of the first sealing surface and the second sealing surface of both the first jaw member and the second jaw member are an electrically conductive surface configured to connect to the electrosurgical energy source.

8. The end effector assembly of claim 1 further comprising at least one non-conductive stop positioned on either side of the blade slot.

9. The end effector assembly of claim 1 further comprising one or more first non-conductive stops positioned on one side of the blade slot and one or more second non-conductive stops positioned on the other side of the blade slot, the first non-conductive stops having a different thickness than the second non-conductive stops.

10. A forceps comprising:
    at least one shaft that includes an end effector assembly at a distal end thereof, the end effector assembly including:
    a first jaw member with a first sealing surface and a second sealing surface;
    a second jaw member with a first sealing surface and a second sealing surface, the first jaw member and the second jaw member being movable relative to each other between an open position and a closed position, the first jaw member and the second jaw member including a blade slot defined therein and extending substantially along the first jaw member and the second jaw member, the first sealing surfaces being positioned on an opposite side of the blade slot than the second sealing surfaces; and
    a cutting blade that reciprocates in the blade slot,
    wherein when the first jaw member and the second jaw member are separated by a first gap having a first maximum gap thickness extending continuously from the blade slot to a first lateral side of the first and second jaw members and the second sealing surface of the first jaw member and the second sealing surface of the second jaw member are separated by a second gap having a second maximum gap thickness extending continuously from the blade slot to a second lateral side of the first and second jaw members, the second maximum gap thickness being larger than the first maximum gap thickness.

11. The forceps of claim 10 wherein the blade slot is closer to the second lateral side of the second gap.

12. The forceps of claim 10 wherein the blade slot is closer to the first lateral side of the first gap.

13. The forceps of claim 10 wherein the first jaw member and the second jaw member rotate relative to each other.

14. The forceps of claim 10 wherein at least one of the first sealing surface and the second sealing surface of at least one of the first jaw member and the second jaw member is an electrically conductive surface configured to connect to an electrosurgical energy source that generates energy to coagulate tissue grasped between the first jaw member and the second jaw member.

15. The forceps of claim 14 wherein both of the first sealing surface and the second sealing surface of at least one of the first jaw member and the second jaw member are an electrically conductive surface configured to connect to the electrosurgical energy source.

16. The forceps of claim 15 wherein both of the first sealing surface and the second sealing surface of both the first jaw member and the second jaw member are an electrically conductive surface configured to connect to the electrosurgical energy source.

17. The forceps of claim 10 further comprising at least one non-conductive stop positioned on either side of the blade slot.

18. The forceps of claim 10 further comprising one or more first non-conductive stops positioned on one side of the blade slot and one or more second non-conductive stops positioned on the other side of the blade slot, the first non-conductive stops having a different thickness than the second non-conductive stops.

19. A method of using forceps, the method comprising:
    opening a first jaw member and a second jaw member, the first jaw member having a first sealing surface and a second sealing surface and the second jaw member having a first sealing surface and a second sealing surface, the first jaw member and the second jaw member including a blade slot defined therein and extending substantially along the first jaw member and the second jaw member, the first sealing surfaces being positioned on an opposite side of the blade slot than the second sealing surfaces;
    closing the first jaw member and the second jaw member to grasp tissue therebetween, when the first jaw member and the second jaw member are in the closed position, the first sealing surface of the first jaw member and the first sealing surface of the first jaw member being separated by a first gap having a first maximum gap thickness extending continuously from the blade slot to a first lateral side of the first and second jaw members and the second sealing surface of the first jaw member and the second sealing surface of the second jaw member are separated by a second gap having a second maximum gap thickness extending continuously from the blade slot to a second lateral side of the first and second jaw members, the second maximum gap thickness being larger than the first maximum gap thickness such that a first maximum compression formed along the first gap is greater than a second maximum compression formed along the second gap; and
    moving a cutting blade along the blade slot to cut the tissue grasped between the first jaw member and the second jaw member.

20. The forceps of claim 19 wherein the blade slot is closer to the second lateral side of the second gap.

21. The forceps of claim 19 wherein the blade slot is closer to the first lateral side of the first gap.

22. The method of claim 19 wherein at least one of the first sealing surface and the second sealing surface of at least one of the first jaw member and the second jaw member is an electrically conductive surface connected to an electrosurgical energy source.

23. The method of claim 22 further comprising generating electrical energy from the electrosurgical energy source to coagulate tissue grasped between the first jaw member and the second jaw member.

24. The method of claim 23 wherein both of the first sealing surface and the second sealing surface of at least one of the first jaw member and the second jaw member are an electrically conductive surface configured to connect to the electrosurgical energy source.

25. The method of claim 24 wherein both of the first sealing surface and the second sealing surface of both the first jaw member and the second jaw member are an electrically conductive surface configured to connect to the electrosurgical energy source.

* * * * *

UNITED STATES PATENT AND TRADEMARK OFFICE
CERTIFICATE OF CORRECTION

PATENT NO. : 11,065,049 B2
APPLICATION NO. : 15/809256
DATED : July 20, 2021
INVENTOR(S) : Wang et al.

Page 1 of 1

It is certified that error appears in the above-identified patent and that said Letters Patent is hereby corrected as shown below:

In the Claims

In Column 10, Line 41, in Claim 20, delete "forceps" and insert --method-- therefor In Column 10, Line 43, in Claim 21, delete "forceps" and insert --method-- therefor Signed and Sealed this
Nineteenth Day of October, 2021

Drew Hirshfeld
*Performing the Functions and Duties of the
Under Secretary of Commerce for Intellectual Property and
Director of the United States Patent and Trademark Office*